(12) United States Patent
Persson

(10) Patent No.: US 6,287,868 B1
(45) Date of Patent: Sep. 11, 2001

(54) PROCESS FOR DETERMINATION OF NITROGEN

(75) Inventor: Jan-Åke Persson, Nyhamnsläge (SE)

(73) Assignee: Foss Tecator AB, Höganäs (SE)

( * ) Notice: Subject to any disclaimer, the term of this patent is extended or adjusted under 35 U.S.C. 154(b) by 0 days.

(21) Appl. No.: 09/362,722

(22) Filed: Jul. 29, 1999

Related U.S. Application Data

(63) Continuation of application No. PCT/SE98/00090, filed on Jan. 22, 1998.

(30) Foreign Application Priority Data

Jan. 29, 1997 (SE) .................................................... 9700249

(51) Int. Cl.$^7$ .................................................... G01N 31/00
(52) U.S. Cl. .......................................... 436/114; 436/163
(58) Field of Search ..................................... 436/114, 163

(56) References Cited

U.S. PATENT DOCUMENTS

| | | | |
|---|---|---|---|
| 2,820,699 | * | 1/1958 | Morris ..................................... 23/230 |
| 3,178,265 | * | 4/1965 | Ferrari ..................................... 23/230 |
| 3,335,097 | * | 8/1967 | Gillis ..................................... 252/428 |
| 3,363,990 | * | 1/1968 | Blom et al. ............................. 23/230 |
| 3,905,770 | | 9/1975 | Mossberg . |
| 4,081,345 | * | 3/1978 | Tolg et al. ............................. 204/195 |
| 4,229,180 | * | 10/1980 | Christoffersen et al. ............... 23/230 |
| 4,645,745 | * | 2/1987 | Hach ..................................... 436/114 |
| 4,645,746 | * | 2/1987 | Hach ..................................... 436/115 |
| 5,968,835 | * | 10/1999 | Aoki et al. ............................. 436/110 |

* cited by examiner

*Primary Examiner*—Jill Warden
*Assistant Examiner*—Monique T. Cole
(74) *Attorney, Agent, or Firm*—Browdy and Neimark

(57) ABSTRACT

A process is claimed for the determination of nitrogen content in a nitrogen containing material, said process comprising: a) at least one pre-treatment step, b) at least one distillation step and c) at least one determination step; wherein said distillation step (a) comprises the substeps of: i) diluting a pre-treated sample of a nitrogen containing material with at least one diluting fluid, ii) inputting steam for commencement of steam distillation, and iii) adding at least one alkali compound, whereby the addition of alkali is made 1–60 seconds after commencement of said inputting of steam and said steam distillation and whereby distillate produced during said steam distillation is recovered in an acidic and/or complexing medium.

20 Claims, No Drawings

PROCESS FOR DETERMINATION OF NITROGEN

CROSS REFERENCE TO RELATED APPLICATION

The present application is a continuation of PCT/SE98/00090, filed Jan. 22, 1998.

The present invention relates to a process for determination of nitrogen, primarily Kjeldahl nitrogen, using an equipment which substantially comprises a multiple step working order. The working order comprises, besides sample preparation, an pre-treatment, such as digestion, of a sample of a nitrogen containing material, followed by distillation and determination/analysis of the nitrogen content, determination of to said nitrogen content directly related amounts of one or more compounds and/or determination of to said nitrogen content directly related analytical parameters. Said determination/analysis is suitably performed gravimetrically, volumetrically and/or chromatographically. More specifically, the process of the present invention refers to a new sequence of the substeps of said distillation, whereby a number of surprising advantages, such as increased operational security and increased analytical accuracy, are obtained.

The Kjeldahl method for determination of nitrogen was introduced in 1883 and has since been subject to substantial development efforts with the aim of improving said method. Determination of nitrogen according to Kjeldahl is today one of the most frequently used analytical methods for analysis of raw materials and final products within for instance the food and forage industry. The chemical principle behind the Kjeldahl method can in short be said to comprise a digestion step carried out at a high temperature, whereby a nitrogen containing sample, such as a protein, in the presence of an acidic reagent, usually comprising sulphuric acid, and a catalyst is transformed into ammonium ions. The sample is subsequently cooled and alkali is added to the digested sample, whereby said ammonium ions are transformed into gaseous ammonia and recovered as such during a distillation. The amount of distilled ammonia is finally determined, for instance titrimetrically. In modern high capacity laboratories are nowadays instruments designed to automatically perform said digestion, distillation and analysis normally used. These instruments provide increased capacity and operational security as well as release operators time due to extended unattended operations.

A typical working sequence when determining nitrogen according to Kjeldahl and using a commercially available equipment is digestion, distillation and titration and can be exemplified as follows. A prepared sample of a nitrogen containing material is weighed into a 100–1000 ml digestion tube in an amount of 0.1–0.5 g followed by addition of 5–20 ml of an acidic reagent, normally concentrated sulphuric acid, and 3–9 g of a catalyst/salt mixture. The catalyst/salt mixture can for instance comprise potassium salts, such as potassium sulphate, in combination with copper and/or selenium and optionally a peroxide, such as hydrogenperoxide. The digestion tube is normally a cylindrical tube (a so called Kjeldahl tube) made of heat resistant glass. Digestion is normally performed at a temperature of 300–600° C., such as 400–500° C. or preferably ~420° C., during for example 45–120 minutes. The digestion involves a chemical reaction wherein bonded nitrogen or nitrogen otherwise included in the material sample is transformed into ammonium ions. The material sample with added reagent and salt/catalyst is sometimes put on hold before distillation. A certain degree of digestion (chemical reaction) occurs, despite the lack of heating, during this hold. A certain amount, such as 2–15 ml, of acid is normally present in the digestion mixture after completed digestion. The digested sample is normally a liquid (acidic solution), but acidic salt crusts are sometimes formed during cooling of the sample. The digestion conditions can within certain limits be adjusted to avoid formation of said salt crusts. The use of high amounts of acid normally result in a liquid solution also after cooling. The disadvantages using high amounts of acid are obvious and comprise increased energy consumption, increased raw material costs, increased costs for waste disposal, hygienic problems related to handling of concentrated acid and reduced analytical accuracy and operational security. The tube containing the digested sample is subsequent the digestion transferred to a distillation equipment and most often diluted with for instance water. The dilution is primarily made to reduce the acid strength in the digested sample. The dilution is in simpler equipment made manually and in more sophisticated equipment by means of an automatic control system. Alkali, such as sodium or potassium hydroxide, is now added to increase the pH value from ~0 to more than 10, preferably ~12. Heat is developed when alkali is added to the sample, which despite the dilution is strongly acidic, and the solutions are normally allowed to mix, at least partly, before distillation. Distillation, most often an steam distillation, is then commenced and obtained ammonia containing distillate is recovered, suitably in an acidic and/or complexing medium such as boric acid. Determination of ammonia, protein and nitrogen, that is Kjeldahl nitrogen, is performed titrimetrically, so called acid-base titration.

Standard methods, such as ISO, CEN, SIS, AOAC, etc., for determination of Kjeldahl nitrogen are normally adapted to manual handling of samples. These methods basically follow above disclosed procedure, including the substeps of the distillation step. The same is valid for control systems used in commercially available automatic equipment. The process steps and substeps is always performed in below sequence:

a) Sample pre-treatment, normally digestion,
b) Distillation comprising the substeps:
   a) Dilution,
   b) Alkali addition,
   c) Distillation, such as steam distillation,
c) Determination/analysis.

Above procedure performed according to for instance any of the standard methods comprises a number of drawbacks and hazards. Dilution with water means that the operator mixes the digested and highly acidic sample with water. The hazards of mixing water and strong acids are well known, such formation of layers and major differences in concentration between said layers. Acid containing salt crusts formed during the digestion are only to a minor degree influenced by water addition. It takes a substantial amount of time to dissolve said salt crusts under conditions existing in a digestion and/or distillation tube. Addition of alkali is in commercially available Kjeldahl equipment normally performed in a closed system, by means of for instance a pump, during 15–30 seconds. The degree of mixing is dependent on for instance the pump used for alkali addition. Added alkali is normally slowly descending towards the bottom of the tube, forming interfacial layers, and if a salt crust is formed during the digestion towards the liquid layer beneath the salt crust. Addition of alkali is uncertain and a heavy heat generating reaction may occur between acid and alkali. The alkali solution has a tendency to form a layer beneath the water diluted sample solution, why a large excess of alkali will be added before reaction between alkali and acid occurs. The heat generated by reaction between alkali and acid is proportional to the amount of acid remaining in the digested sample. The subsequent step, the distillation step, is normally commenced 5–30 seconds after the alkali addition. The acid containing digested sample solution and the alkali solution arc during said 5–30 seconds mixed to a certain degree through mainly diffusion processes in the interface between these solutions. Inlet of steam for steam distillation implies a rapid mixing of the acidic sample and the alkali with pendant increased temperature. A large acid excess or the presence of salt crusts may give rise to a heavy and even hazardously heavy reaction. Alkali and/or sample may escape the tube due to tube cracking or activation of safety lock gates and the like. These risks are well known to users of commercially available Kjeldahl equipment, why many users dilute the sample manually whereby a more efficient mixing can be obtained which reduces the heavy reaction caused by rapid mixing during the inlet of steam. Manual dilution is performed when the tube still is warm after the sample digestion, which implies handling hazards. The heavy reaction between the acidic sample and the alkali as disclosed above furthermore generates gases such as steam and ammonia as well as a sudden and turbulent mixing of the liquids. This often results in a shock wave through the entire equipment and through the acidic and/or complexing medium (boric acid solution) used for ammonia recovery during the distillation. There is thus an obvious risk of loss of ammonia and/or recovery medium with pendent incorrect analytical yield.

The present invention makes it quite unexpectedly possible to avoid disclosed drawbacks and problems related to nitrogen determination according to for instance Kjeldahl. The present invention comprises a completely new working sequence in regard of the substeps in the distillation step. The step and substeps of the present invention comprises (a) pre-treatment, such as said digestion of a sample of a nitrogen containing material, (b)(i) dilution of the pre-treated sample with for instance water or a weak aqueous alkali solution giving a sample pH of 7–9, (b)(ii) inlet of steam and commencement steam distillation, (b)(iii) addition of alkali, preferably as an aqueous solution and (c) determination/analysis by for instance titration. The alkali in the weak alkali solution added in step (b) substep (i) and the alkali added in step (b) substep (iii) are suitably an alkali metal hydroxide, such as potassium and/or sodium hydroxide. Step (b) substep (ii) gives a thorough mixing of the digested and acidic sample and the diluting liquid added in step (b) substep (i) and disintegration and solution of possible salt crusts formed during the pre-treatment/digestion. Inlet of steam is always commenced before addition of alkali according to step (b) substep (iii), which implies a thorough mixing and minimised formation of layers having different acid or alkali concentrations. A suitable time difference between substeps (ii) and (iii) of step (b) is within the interval 1–60 seconds. There will, should the time period between initiating said substeps (ii) and (iii).be too long, be a certain risk of over heating said pre-treated/digested and diluted sample during the addition of alkali. The risk is related to the heat generated by reaction between acid and alkali during said step (b) substep (iii). The time difference between said substeps (ii) and (iii) of step (b) is suitably less than 60 seconds, preferably less than 30 seconds such as 2–20 or 2–5 seconds. The alkali addition, suitably in the form of an aqueous solution of potassium and/or sodium hydroxide, is continued until the pH value of obtained mixture of digested and diluted sample and added alkali reaches a value of 10–14, preferably 11–13 and most preferably 12±0.2. Said pH value should, in order to obtain as accurate an analytical result as possible, not be less than 10. Addition of alkali is substantially performed synchronised with inlet of steam whereby said inlet of steam provides a continuous mixing and whereby layers having different acid and alkali concentrations is avoided. The distillate formed during step (b) is suitably recovered by means of conventionally used methods, for instance in an acidic and/or ammonia complexing medium such as an aqueous solution of boric or sulphuric acid. Step (c) comprises a determination/analysis, which suitably is performed according to known gravimetric, volumetric, chromatographic etc. procedures, such as titration.

The process according to the present invention is very suitable for determination of nitrogen according to Kjeldahl including determination of to said nitrogen directly related compounds and/or analytical parameters. Compounds which can be directly related to said nitrogen can be exemplified by proteins, amines and amino acids as well as by nitrogen containing compounds such as ammonium, urea, nitro, azo, hydrazo compounds, nitrates and nitrites.

The sequence of substeps in the distillation step of the present invention is furthermore suitable to be included in processes for determination of compounds such as cyanides and phenols.

The process of the present invention comprises a pre-treatment step. A pre-treatment may comprise mixing a nitrogen containing material with an acidic reagent followed by digestion at a temperature of 300–600° C., preferably 400–500° C. and most preferably 400–450° C., or mixing a nitrogen containing material with an acidic reagent at a temperature of 0–50° C., preferably 20–25° C., followed by a hold at said temperature until distillation can be performed with requested effect. The process of the present invention furthermore comprises at least one determination or analysis as previously disclosed, such as a titration.

The advantages obtained with the process according to the present invention arc multiple and can be summarised
i) gradual disintegration and solution during the distillation step of salt crusts,
ii) minimised or substantially reduced sudden and turbulent mixing of the liquids and pendant shock waves through used equipment,
iii) improved handling security and reduced hazards related to damages of the equipment,
iv) improved analytical accuracy and operational security.

The utility and application of the process according to the present invention are highly improved compared to conventionally used processes wherein large amounts of acidic reagents, such as sulphuric acid, are present. A wider acidic interval can be used with high analytical accuracy (correct nitrogen yield), which is an advantage in many standard methods, such as ISO, IDF, AOAC etc., which methods require or demand analytical conditions wherein large amounts of acidic reagents are used.

These and other objects and the attendant advantages will be more fully understood from the following detailed description, taken in conjunction with embodiment Examples 1–3, wherein Example 1 teaches an embodiment of the present invention used for determination of Kjeldahl nitrogen, Example 2 (comparative example) teaches a conventionally known process for said determination and Example 3 refers to nitrogen yields obtained according to the process of the present invention and according to a conventionally used process. Said nitrogen yields are presented as a graph (Graph 1). While particular embodiments of the invention are shown, it will be understood, of course, that the invention is not limited thereto since many modifications may be made, and it is, therefore, contemplated to cover by the appended Claims any such modifications as fall within the true spirit and scope of the invention.

EXAMPLE 1

Digestion: 1.000 g of a homogeneous nitrogen containing sample of a grain product was weighed into a digestion tube, a so called Kjeldahl tube. 12 ml of concentrated sulphuric acid and a catalyst/salt mixture consisting of 7.0 g of $K_2SO_4$ and 0.8 g of $CuSO_4.5\ H_2O$ were added to the sample. The digestion tube was transferred to a heating block and digestion was during 60 minutes carried out at a temperature of 420° C. Acid was through chemical reactions with the sample and the catalyst/salt mixture consumed during the digestion. 20 samples were simultaneously digested in a rack system. The samples were after completed digestion cooled. Approximately 75% of the samples formed during the cooling salt crusts at the bottom of the tubes. The nitrogen in the sample material was now present as ammonium ions.

Distillation: The digestion tube containing the digested sample was connected to a distillator. 70 ml of water was initially added to dilute the remaining acid. Steam was now let in and steam distillation commenced. Salts crusts were disintegrated and gradually dissolved. 50 ml of a 40%-w/w aqueous sodium hydroxide solution was 2 seconds later added to increase the pH value to more than 10. The ammonium ions were at this high pH value transformed into ammonia and formed ammonia was steam distilled to a collector containing 25 ml of a 4%-w/w aqueous boric acid solution. The boric acid solution contained a pH indicator (bromocresol green/methyl red). A total volume of 150 ml was distilled to the collector. The boric acid formed complexes with the ammonia.

Titration and calculation: Determination of nitrogen was carried out by means of an acid-base titration using 0.2000 M HCl. Consumed acid was related to the nitrogen content of the sample material using below mathematical formula:

$$N = \frac{(T - B) \times (N \times 14.007 \times 100\%}{\text{Sample weight in mg}}$$

T=Sample titration
B=Blank titration
N=Normality of titrant

Protein determination was made by multiplying above obtained results with an empirical protein factor according to below:

% protein=% N×F
F=Protein factor (normally 6.25)

EXAMPLE 2

Digestion: As in Example 1 with results similar thereto.

Distillation: The digestion tube containing the digested sample was connected to a distillator. 70 ml of water was initially added to dilute the remaining acid followed by addition of 50 ml of a 40%-w/w aqueous sodium hydroxide solution to increase the pH value to more than 10. Salt crusts were not or only to a very small extent affected by addition of water and/or sodium hydroxide solution. The ammonium ions were at this high pH value transformed into ammonia. Steam was 5 seconds after addition of sodium hydroxide let in and steam distillation commenced. Formed ammonia was steam distilled to a collector containing 25 ml of a 4%-w/w aqueous boric acid solution. The boric acid solution contained a pH indicator (bromocresol green/methyl red). A total volume of 150 ml was distilled to the collector. The boric acid formed complexes with the ammonia.

Titration and calculation: As in Example 1.

EXAMPLE 3

Nitrogen yield during distillation and titration according to the present invention (Example 1) and according to a conventionally used process (Example 2) was determined by means of a known amount of nitrogen, in the form of ammonium sulphate, added to 0–18 ml of sulphuric acid. The results were after distillation and titration on calculated and plotted as a graph.

What is claimed is:

1. Process for determination of nitrogen content, in a nitrogen containing material, said process comprising
   (a) at least one pre-treatment step, (b) at least one distillation step and (c) at least one determination step
   wherein said distillation step (a) comprises the substeps of
   i) diluting a pre-treated sample of a nitrogen containing material with at least one diluting fluid,
   ii) inputting steam for the commencement of steam distillation, and
   iii) adding at least one alkali compound,
   whereby the addition of alkali is made 1–60 seconds after commencement of said inputting of steam and said steam distillation and whereby distillate produced during said steam distillation is recovered in an acidic and/or complexing medium.

2. Process according to claim 1 wherein the diluting fluid in substep (i) is water.

3. Process according to claim 1 wherein the diluting fluid in substep (i) is an aqueous alkali solution giving a pH value of 7–9.

4. Process according to claim 1 wherein the alkali compound added in substep (iii) is added 2–20 seconds after commencement of steam distillation.

5. Process according to claim 1 wherein the alkali compound added in substep (iii) is added 2–5 seconds after commencement of steam distillation.

6. Process according to claim 1 wherein the alkali compound added in substep (iii) is added as an aqueous solution.

7. Process according to claim 1 wherein the alkali compound added in substep (iii) is potassium and/or sodium hydroxide.

8. Process according to claim 1 wherein the alkali compound added in substep (iii) is added in an amount giving a pH value of 10–14.

9. Process according to claim 1 wherein the alkali compound added in substep (iii) is added in an amount giving a pH value of 12±0.2.

10. Process according to claim 1 wherein the compound directly related to said nitrogen is a protein, an amine or an amino acid.

11. Process according to claim 1 wherein the compound directly related to said nitrogen is an ammonium, a urea, a nitro, an azo or a hydrazo compound.

12. Process according to claim 1 wherein the acidic and/or complexing medium in which said distillate is recovered, is boric or sulphuric acid.

13. Process according to claim 12 wherein the boric or sulphuric acid is present as an aqueous solution.

14. Process according to claim 1 wherein the pretreatment step (a) comprises mixing a sample of a nitrogen containing material with an acidic reagent followed by digestion of said sample at a temperature of 300–600° C.

15. Process according to claim 1 wherein the pretreatment step (a) comprises mixing a sample of a nitrogen containing material with an acidic reagent at a of 0–50° C.

16. Process according to claim 1 wherein the determination step (c) comprises at least one titration.

17. Process according to claim 16 wherein the at least one titration is at least one acid-base titration.

18. Process according to claim 1, wherein the pretreatment step is a digestion step.

19. Process according to claim 18, wherein the alkali compound added in substep (iii) is added 1–30 seconds after commencement of steam distillation.

20. Process according to claim 19, wherein the alkali compound added in substep (iii) is added in an amount giving a pH value of 11–13, and said digestion step is carried out at a temperature of 400–500° C.

* * * * *